US008208619B2

(12) United States Patent  
Perrin et al.

(10) Patent No.: US 8,208,619 B2  
(45) Date of Patent: Jun. 26, 2012

(54) METHOD AND APPARATUS FOR IMPROVING CALL YIELDS WHEN CONTACTING PATIENTS WHO ARE DUE FOR A VISIT BUT DO NOT HAVE A SCHEDULED APPOINTMENT

(75) Inventors: Brian William Perrin, American Fork, UT (US); Brett Cornell Gerlach, Eagle Mountain, UT (US)

(73) Assignee: Brevium, Inc., Eagle Mountain, UT (US)

( * ) Notice: Subject to any disclaimer, the term of this patent is extended or adjusted under 35 U.S.C. 154(b) by 1188 days.

(21) Appl. No.: 11/963,823

(22) Filed: Dec. 22, 2007

(65) Prior Publication Data

US 2009/0161846 A1 Jun. 25, 2009

(51) Int. Cl.  
*H04M 3/00* (2006.01)  
*H04M 5/00* (2006.01)

(52) U.S. Cl. .................. 379/266.08; 379/266.07; 379/51

(58) Field of Classification Search ...................... 379/51  
See application file for complete search history.

(56) References Cited

U.S. PATENT DOCUMENTS

| | | | |
|---|---|---|---|
| 5,737,726 A | 4/1998 | Cameron et al. | |
| 5,918,208 A | 6/1999 | Javitt | |
| 5,982,863 A | 11/1999 | Smiley et al. | |
| 6,024,699 A | 2/2000 | Surwit et al. | |
| 6,088,429 A | 7/2000 | Garcia | |
| 7,702,522 B1 | 4/2010 | Sholem | |
| 2002/0138306 A1 | 9/2002 | Sabovich | |
| 2002/0156672 A1 | 10/2002 | Burko | |
| 2003/0195774 A1 | 10/2003 | Abbo | |
| 2004/0019501 A1 | 1/2004 | White et al. | |
| 2004/0181433 A1 | 9/2004 | Blair | |
| 2004/0243436 A1 | 12/2004 | Rawat et al. | |

(Continued)

OTHER PUBLICATIONS

Corey, David J., "Appointment Standardization Integrated Program Team Meeting-Activation of MCP Status." Department of Defense-Tricare Management Activity, Oct. 24, 2000, 22 Pages.

(Continued)

*Primary Examiner* — Alexander Jamal  
(74) *Attorney, Agent, or Firm* — Scheinberg & Associates, PC; Michael O. Scheinberg; John B. Kelly

(57) ABSTRACT

A method and apparatus for improving call yields and reducing redundant calls while contacting patients who have not responded to reminders to schedule a return appointment, or who are due for a visit according to accepted standards of care or office policies, but have not scheduled an appointment. The patient reactivation system is queried for the next patient on the contact list, and queried again to find all patients sharing one or more phone numbers with this patient. Information required for contacting these patients to invite them to make an appointment is displayed. The user is presented one phone number at a time, and prompted to call this number and invite all listed patients to make an appointment. Results are collected, and when multiple patients are displayed, the program may prompt the user for clarification regarding which patients a given result applies to. Based on the results collected, the system determines whether or not to prompt the user to call the same patients again with other phone numbers, if available. Finally, the system analyzes the set of results collected in order to calculate follow-up call times for each patient. The system may keep separate follow-up call times for each phone number as well in order to further improve the patient experience.

19 Claims, 9 Drawing Sheets

U.S. PATENT DOCUMENTS

| | | | |
|---|---|---|---|
| 2005/0234739 | A1 | 10/2005 | Schoenberg |
| 2006/0047552 | A1 | 3/2006 | Larsen et al. |
| 2006/0047553 | A1 | 3/2006 | Fuhrmann et al. |
| 2006/0047554 | A1 | 3/2006 | Larsen et al. |
| 2006/0053044 | A1 | 3/2006 | Kurian et al. |
| 2007/0078697 | A1 | 4/2007 | Nixon |
| 2008/0306781 | A1 | 12/2008 | Gerlach et al. |
| 2009/0055220 | A1* | 2/2009 | Rapaport et al. .......... 705/2 |
| 2009/0094054 | A1 | 4/2009 | Perrin et al. |

OTHER PUBLICATIONS

Health Systems Management Group, "Medical Practice Expert Software Features," Webpages, 2005, Exact publication date unknown, Retrieved Apr. 26, 2010, [http//web.archive.org/web/20050324141543/www.hsmg.biz/cal.med/features/html/], 9 Pages.

CPM Marketing Group, Inc., "Life Connections," Webpages, 2006, Exact publication date unknown, Retrieved Apr. 26, 2010, [http://web.archive.org/web/20060308193454/www.cpm.com/physicians/solutions/corecomm.cfm], 8 Pages.

Frieden, Joyce, "Electronic Health Records Yield Business Payoff," Internal Medicine News, Jan. 15, 2006, p. 76, vol. 39, No. 2, p. 76, ISSN 1097-8690, pp. 10-11.

Telapatient.Com, "PowerCalls-DDS Appointment Confirmation System," Webpages, 1985, Exact publication date unknown, Retrieved Nov. 19, 2009, [http:/www.telapatient.com/pcalls.html], 5 Pages.

American Academy of Pediatrics, "Vaccine Reminder Recall System: A Practical Guide for Pediatric Practices," Webpages, Jun. 1984, Timeline for Implementation, Aug. 1989 Complete Electronic Medical Record, [http://practice.aap.org], 5 pages.

Elexity.com; 2004-2007; Elexity; retrieved Jun. 9, 2009 [www.elexity.com; http://web.archive.org/web/20070920075315/www.elexity.com/generalSite/solutionsApptReminders.asp].

Phytel.com; 2004; Phytel; retrieved Jun. 9, 2009 [www.phytel.com; http://web.archive.org/web/20041021033228/phytel.com/solutions/appointmentconfirmations.html].

SMILEREMINDER.COM, Webpages, 2002, Retrieved Sep. 17, 2009, [http://web.archive.org/web/20021210135102/www.smilereminder.com/index.html], 3 Pages.

PHYTEL.COM, Brochure, 2002, Exact publication date unknown, Retrieved Sep. 17, 2009, [http://web.archive.org/web/20030407162143/phytel.com/brochure.pdf], 6 Pages.

PHYTEL.COM, Webpages, 2006, Exact publication date unknown, Retrieved Sep. 17, 2009, [http://web.archive.org/web/20060813164142/http://www.phytel.com], 4 Pages.

PHYTEL.COM, Webpages, 2007, Exact publication date unknown, Retrieved Sep. 17, 2009, [http://web.archive.org/web/20071024121500/www.phytel.com/products/products01.htm], 3 Pages.

* cited by examiner

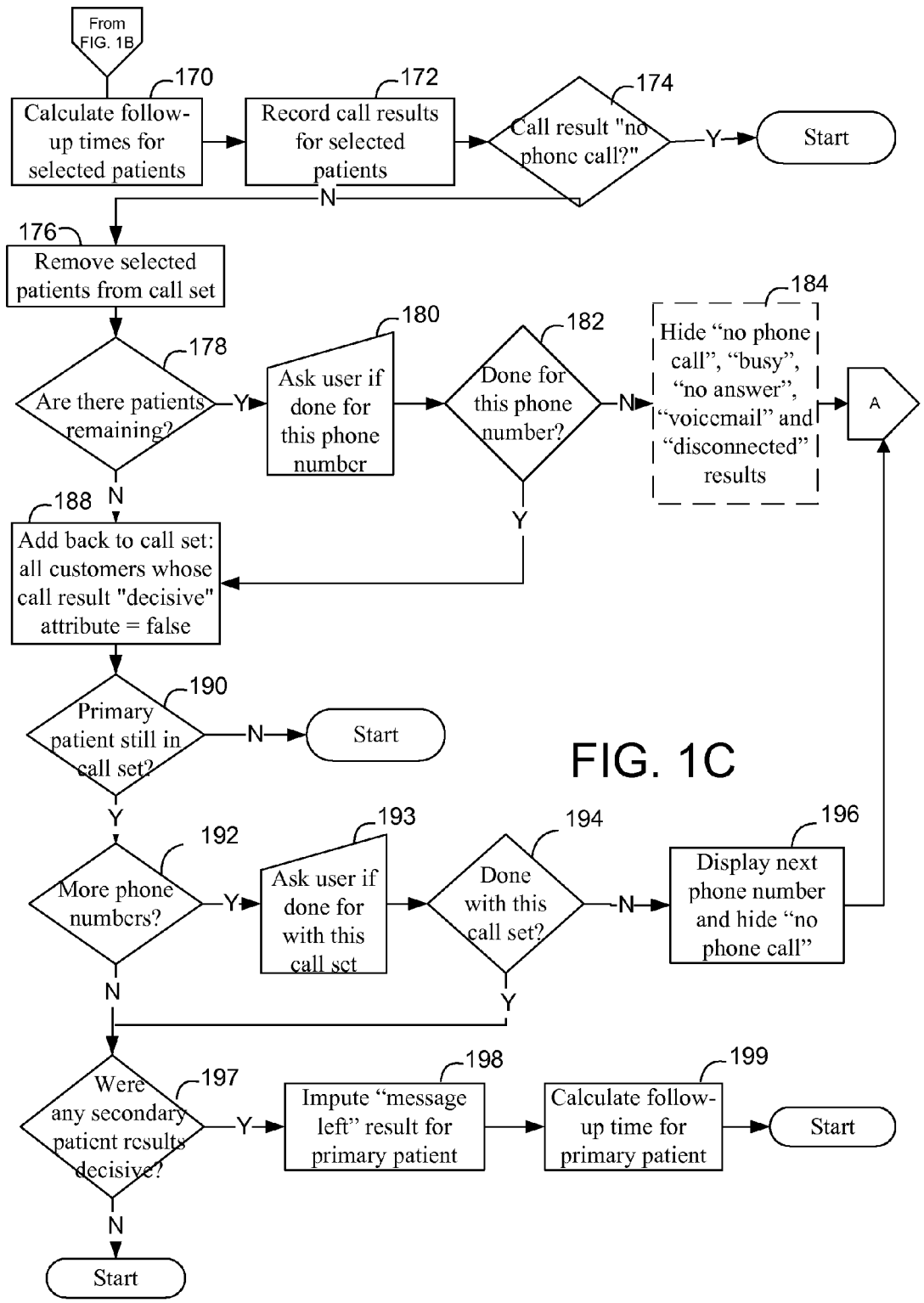

FIG. 2

| Result | Decisive | SelectType | Timeout | Retries |
|---|---|---|---|---|
| No answer | false | 1 | 4.1 | 3 |
| Busy | false | 1 | 1.2 | 5 |
| Voicemail | true | 1 | 24 | 2 |
| Disconnected | false | 1 | 90 | 9 |
| Call back after | true | 3 | NULL (input by user) | 3 |
| Customer will call us later | true | 3 | 28 | 2 |
| Appointment accepted | true | 2 | 14 | 1 |
| Translator needed | false | 3 | 28 | 4 |
| Condition resolved | true | 2 | 21 | 0 |
| Refused care | true | 2 | 21 | 0 |
| Seen by other doctor | true | 2 | 21 | 0 |
| Moved away | true | 3 | 21 | 0 |
| Deceased | true | 2 | 21 | 0 |
| Don't call again | true | 3 | 730 | 1 |
| Don't use this number | false | 2 | 24 | 9 |
| No phone call | true | 0 | 21 | 0 |

FIG. 3

| Name, Insurance | App Due | With | At | For |
|---|---|---|---|---|
| Joe Schmoe | 72 Apr '07 | Beaker | Dallas Eye | Diabetes |
| Medicare | 05/24/06 | Hollywood | IPN | [Postop F/u Visit Incld Global ] |
| Referring physician: | 04/19/06 | Hollywood | IPN | [Destruc Les Choroid-1/> Sessn-] |
| Billy Blazer | 03/22/06 | Hollywood | IPN | [Offic/outpt E&m Estab Low-mod ] |
|  | 03/15/06 | Hollywood | IPN | [Intravitreal Inj-agent (sep Pr) ] |
| Mary Lockheart | 77 Aug '06 | Blazer | Dallas Eye | Full Exam: 1 Year Exam |
| Medicare | 08/26/05 | Blazer | Dallas Eye | [Ophth Serv; Med Exam; Comp Est]... |
|  | 01/14/04 | Blazer | Dallas Eye | [Contact Lens Check No Charge] |
|  | 12/16/03 | Blazer | Dallas Eye | [Ophth Serv; Med Exam; Comp Est] |
| Jane Schmoe | 73 Jan '07 | Blazer | Dallas Eye | Full Exam: 1 Year Exam |
| Medicare | 01/24/06 | Blazer | Dallas Eye | [Ophth Serv; Med Exam; Comp New] mc blue ch ref in sysm, choice |

No prior contact with these patients.

441-421-1111

Call was answered...

| Appointment accepted | Call patient back after... |
|---|---|
| Message left | Patient will call us later |
| Translator needed | Don't use this number |
|  | No, thank you... |

FIG. 4

Brevium Total Recall

| Name / Insurance | Age | Appt Due | With | At | For |
|---|---|---|---|---|---|
| Joe Schmoe | 72 | Apr '07 | | | Diabetes |
| Medicare | | 05/24/06 | Beaker | Dallas Eye | Postop F/u Visit Incld Global ] |
| Referring physician: | | 04/19/06 | Hollywood | IPN | Destruc Les Choroid-1/> Sessn-] |
| Billy Blazer | | 03/22/06 | Hollywood | IPN | [Offic/outpt E&m Estab Low-mod ] |
| | | 03/15/06 | Hollywood | IPN | [Intravitreal Inj-agent (sep Pr.] |
| Mary Lockheart | 77 | Aug '06 | | | Full Exam: 1 Year Exam |
| Medicare | | 08/26/05 | Blazer | Dallas Eye | [Ophth Serv: Med Exam; Comp Est]... |
| | | 01/14/04 | Blazer | Dallas Eye | [Contact Lens Check No Charge] |
| | | 12/16/03 | Blazer | Dallas Eye | [Ophth Serv: Med Exam; Comp Est] b. choice |
| Jane Schmoe | 73 | Jan '07 | | | Full Exam: 1 Year Exam |
| Medicare | | 01/24/06 | Blazer | Dallas Eye | [Ophth Serv: Med Exam; Comp New] mc blue ch ref in sysm |

No prior contact with these patients 441-421-1111

Patient will call us later

Applies to:
☑ Joe Schmoe
☑ Mary Lockheart
☑ Jane Schmoe

Notes:

METHOD AND APPARATUS FOR IMPROVING CALL YIELDS WHEN CONTACTING PATIENTS WHO ARE DUE FOR A VISIT BUT DO NOT HAVE A SCHEDULED APPOINTMENT

TECHNICAL FIELD

The present invention relates to a method and apparatus for internal marketing, and more particularly, to a method and apparatus for facilitating efficient contact with patients who require a follow-up appointment for healthcare.

BACKGROUND OF THE INVENTION

Most healthcare practices rely on scheduled appointments to provide an agreed time and place to serve patients. In many cases, after serving a patient, a return appointment will be recommended for some time in the future. Often, an appointment is made for a return visit before the patient leaves the office. However, if the needed appointment is too far in the future, if staff schedules are unreliable, or if a suitable appointment cannot be found quickly, then the office may choose instead to use a recall. A recall is a notice, sent to the patient prior to the desired appointment date, reminding the patient to call to schedule an appointment.

Many management systems that schedule patient appointments provide support for recall notices. Typically, these systems allow entry of a record consisting of the patient, the target date for the unscheduled appointment, and some notes about the reason for the recall. On a regular basis, the management system is used to generate printed cards, letters, or address labels, so that reminders to call for an appointment can be sent to the appropriate patients. Instead of printed reminders, automated calling systems are sometimes used to leave a recorded message requesting a return call to schedule an appointment.

Unfortunately, many patients fail to respond to recall notices. Consequently, they don't receive the care they need. Practice management systems often provide a list of patients who have not responded to recall notices, so that these patients can be contacted or reminded again. However, these simple lists of unresponsive patients are inadequate for practices that are determined to continue calling until they reach each patient and are either able to schedule an appointment or learn that the patient is unable or unwilling to return for needed care. These practices need to ensure that additional contact attempts are not made until a sufficient time has elapsed to warrant another contact. Further, callers require that as patients are contacted and appointments are scheduled or refused, those patients are deleted from the list so that they are not contacted again.

Another disadvantage of prior art systems is that they provide no guidance on how to use multiple phone numbers when more than one number is available. As a result, a user might not try a second number when appropriate, resulting in a missed opportunity to contact a patient. In cases where the user decides to try two numbers and gets two distinct call results, she is left to herself to decide which call result to record. This can cause the system to place the patient back on the call list either too soon or too late. If too soon, the unnecessary call may generate bad will with the patient. If too late, needed care may be delayed.

Multiple patients often reside at the same household. By contacting one patient at a time, the same household may receive multiple calls from the same organization when one call would have sufficed. This results in bad will with the patient, and a lower average number of appointments made per call, or call yield, thus impacting efficiency and productivity.

Thus, the health care industry needs a system which provides better support for calling overdue patients with multiple phone numbers, as well as households with multiple patients, in order to increase call yields and improve patient satisfaction by properly spacing and eliminating redundant calls.

SUMMARY OF THE INVENTION

An object of the present invention is to improve both call yields and the patient experience when a patient has multiple phone numbers or when there are multiple patients in a household.

In a preferred embodiment, a system of the present invention determines from a practice management database when multiple patients requiring telephone contacts to schedule appointments live in the same household. For example, the system may identify patients having the same telephone number or having certain familial relationships as living in the same household. The system facilitates scheduling appointments with multiple individuals in the same household by making more than one appointment or collecting information about more than one patient in a single call. The system also facilitates contacting patients when the patients provide multiple telephone numbers.

BRIEF DESCRIPTION OF THE DRAWINGS

FIGS. 1A-1C are flowcharts showing a preferred embodiment of a method of the invention.

FIG. 2 is an exemplary user interface, prompting the user to call the first of two phone numbers, to request appointments with three patients at the same household.

FIG. 3 is an exemplary call results table, showing the timeout values, retry counts, and other attributes associated with each call result.

FIG. 4 is an exemplary user interface prompting the user to specify the call result from a call that was answered.

FIG. 5 is an exemplary user interface, prompting the user to specify which patients the indicated call result applies to.

FIG. 6 is an exemplary user interface, prompting the user to determine whether to continue collecting additional call results at the current phone number, or to move on to the next phone number.

DETAILED DESCRIPTION OF PREFERRED EMBODIMENTS OF THE INVENTION

Figure 1A:
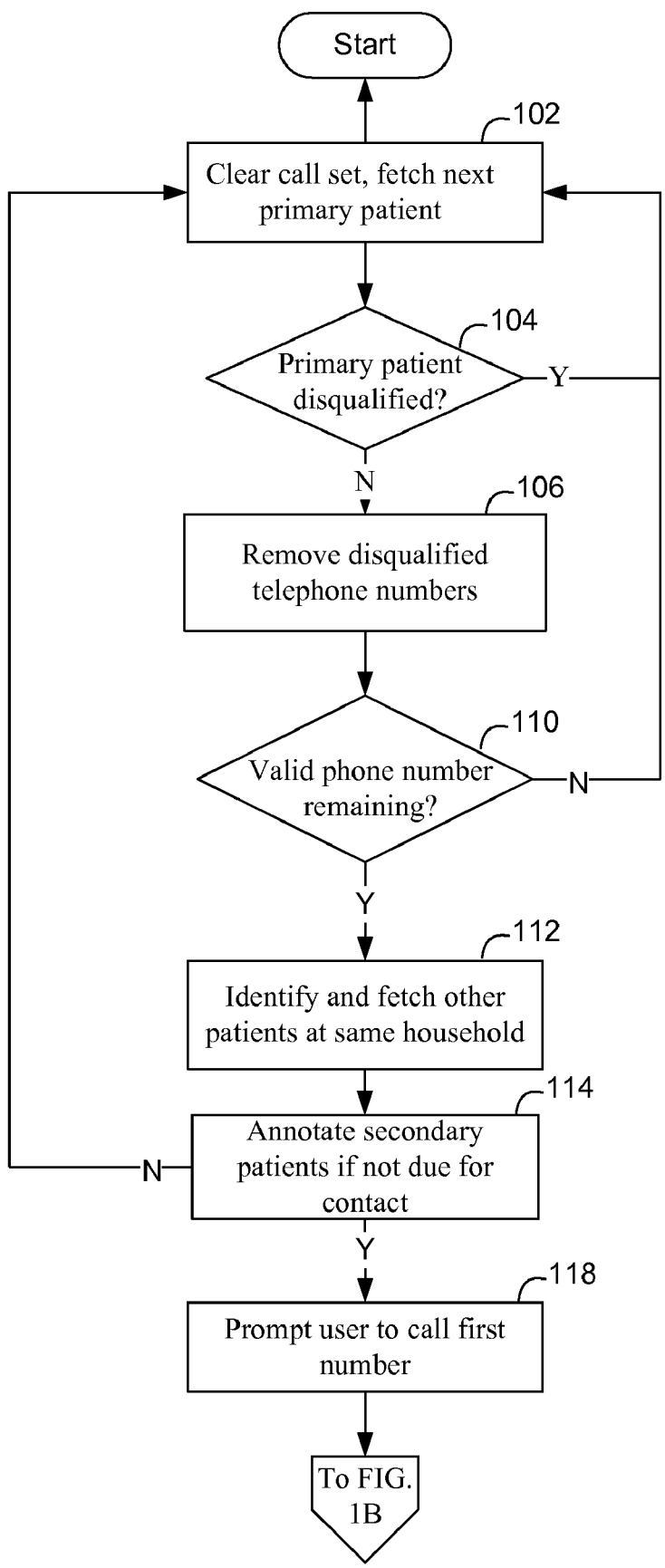
Figure 1B:
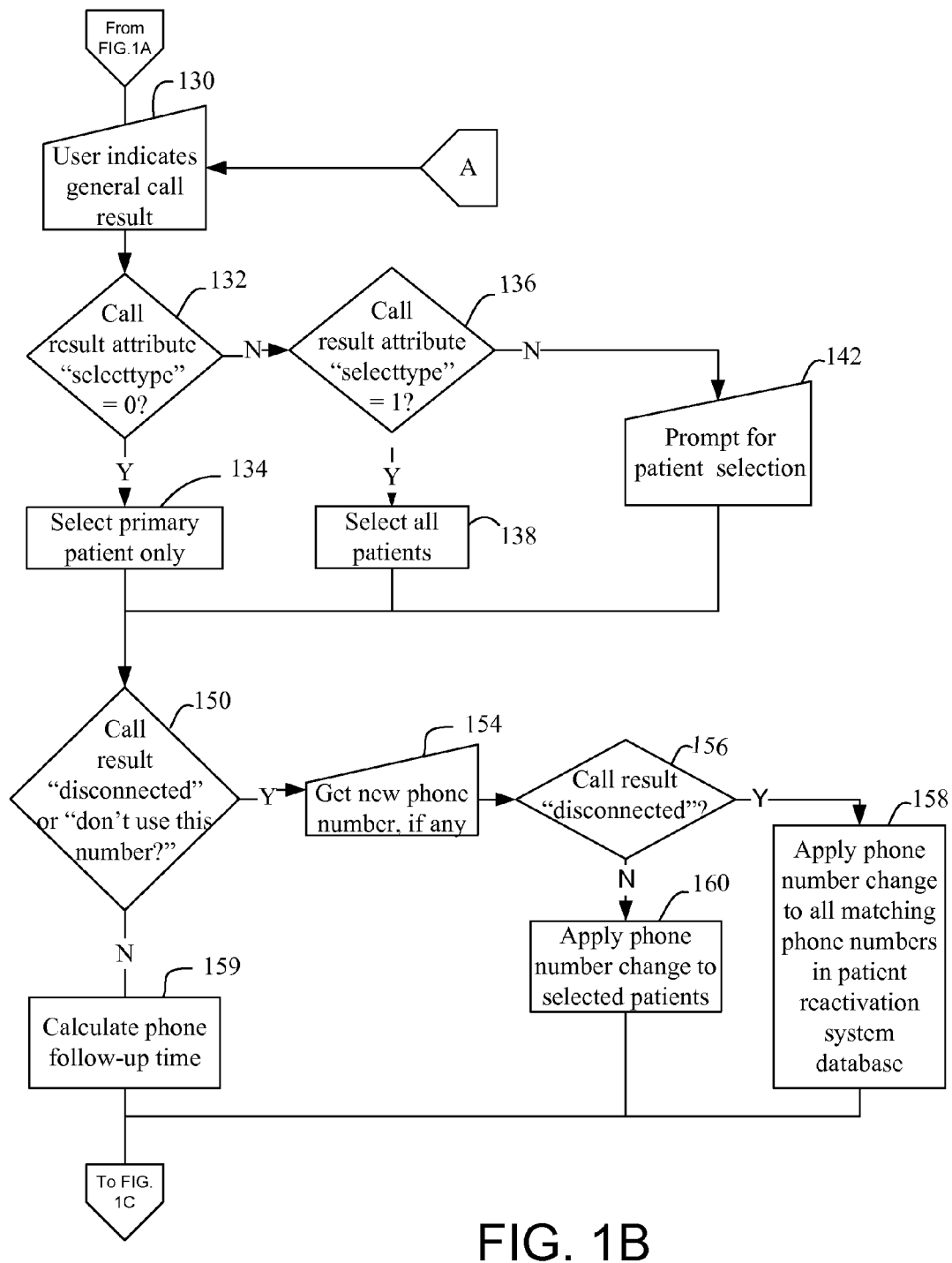

An aspect of some embodiments of the invention improves the patient experience by spacing calls appropriately when patients have provided the organization with multiple phone numbers, and by eliminating redundant calls to multiple patients at the same household.

Another aspect of some embodiments the present invention produces more appointments per call via said patient experience improvements.

Contacting patients who are overdue for care is a cost-effective way of both improving care and increasing revenue by filling available appointments. In a U.S. patent application Ser. No. 11/484,340 for "Method and Apparatus for Identifying and Contacting Customers Who Are Due for a Visit but Have Not Scheduled an Appointment," which was filed Jul. 10, 2006 and is hereby incorporated by reference, Gerlach and Perrin describe a patient reactivation system that analyzes data in practice management systems to identify patients who are overdue for care and need to be contacted to schedule an appointment. The system prompts the user to call one patient at a time, presenting all available phone numbers for that patient, and requires that the user enter one result for each patient before moving on to the next patient. Other improvements are described in U.S. patent application Ser. No. 11/938,087, filed Nov. 9, 2007 and U.S. patent application Ser. No. 11/934,615 filed Nov. 2, 2007, both of which are hereby incorporated by reference.

However, since patients often provide multiple phone numbers to the organizations that provide them care, and since multiple patients often reside at the same household, complications arise when attempting to contact one patient at a time and record an appropriate call result. Unless multiple phone numbers and multiple patients at the same household are handled appropriately, contact intervals will be inappropriate and redundant calls will be made, leading to bad will with patients and reduced call yields.

Various embodiments of the present invention overcome one or more of these difficulties by clearly indicating which phone number should be called next, by identifying and presenting multiple patients thought to reside at the same household so that appointments can be offered to all of them with a single call, and by determining when to call the same patient or the same phone number again when multiple phone numbers are used or multiple patients reside at the same household. The benefits are an improved patient experience and higher call yields.

One preferred method in accordance with the invention begins by fetching and displaying on a computer screen to a user the record for a patient, hereafter referred to as the primary patient, from a contact list. A contact list is a list of all patients who need to be contacted to schedule appointments. The system then queries its contact list to determine all patients residing in the same household as the primary patient. The patients residing with the primary patient are referred to as secondary patients. The selected primary patient and corresponding secondary patients comprise a set of patients that will be contacted as a group, hereafter referred to as the call set. Criteria, such as a common phone number, common address, or a familial relation, may be used to determine the secondary patients to a call set.

To assist the user in making the call, the system displays relevant patient information, such as appointment history, contact history, insurance information, and the health conditions necessitating an appointment. The system then either autodials or prompts the user to call one specific phone number belonging to the primary patient and record the call result. If there are multiple patients in the call set, then based on the call result, the system may prompt for clarification as to which patients that call result applies to, and then allow additional results to be recorded for other patients in the call set. As each call result is recorded, a follow-up time is calculated and stored for each patient associated with that result.

After collecting all results for the first phone number, a follow-up time is calculated and stored for that phone number. This phone number follow-up time is distinct from the follow-up time for specific patients. If another phone number is available for the call set, the system will determine, based on the call results of the first phone number, whether to prompt the user to try the second phone number. If the second phone number is used, a separate call result is recorded for the second phone number as with the first. If there are more phone numbers, the process continues until either all available phone numbers are exhausted or the primary patient is contacted successfully. As each call result is recorded, the follow-up time is updated for the patients associated with each result and for each separate phone number. Finally, the process begins again by clearing the call set and fetching the next patient from the contact list.

The following detailed description will be made in the context of the broad steps of a method. It will be understood that the steps of the method described can be accomplished by means of a conventional computer system, including a display device and one or more input devices, such as a keyboard, mouse or track pad and a telephone or other device for communicating with patients.

The broad steps are: fetch the next primary patient from the contact list and query the contact list for secondary patients. Prompt the user to call the patient(s), beginning with the first phone number. Collect call results for the call set until results are deemed decisive or phone numbers are exhausted. As each call result is collected, calculate the follow-up time for the current phone number and for selected patients.

Preferred implementations of the broad steps are described below in more detail. Some of the steps described below, such as generating calling lists and presenting information to the user, are preferably performed automatically under computer control. That is, those steps are performed by the computer in accordance with programmed instructions and without human intervention. Automatic operation does not exclude a person initiating any step or the entire process. Other steps, such as speaking to patients and entering results are preferably performed by a user.

Fetch the Next Primary Patient from the Contact List and Query the Contact List for Secondary Patients The contact list is a list of patients who, based on guidelines for prior diagnoses and/or office procedures, need to receive care, and who, based on follow-up guidelines for prior contact, are deemed due to be contacted. The contact list may be sorted in various ways in order to first contact patients whose visits have a higher expected value, as described in applicants' copending U.S. patent application Ser. No. 11/484, 340. The contact list is typically rebuilt daily, or immediately when administrative parameters are changed.

Step 102 entails initializing the system by clearing any existing call set and fetching the next patient from the contact list. This is the primary patient for this new call set. In step 104, the management system is queried for disqualifying conditions that would render the fetched patient ineligible for contact. For example, patients who have already made an appointment or who have died are disqualified. If the primary patient is disqualified, the call set is discarded and the process returns to step 102 and begins again by fetching the next primary patient from the contact list.

If the primary patient is qualified, each phone number belonging to the primary patient is checked for disqualifying conditions, such as a follow up time in the future or disconnected. Disqualified numbers are removed from the list in step 106. Decision block 110 shows that if there are no qualified phone numbers remaining, the process starts again with a new patient in step 102. If at least one valid phone number is available, the contact list is then queried in step 112 to identify other patients in the same household who are also due for contact. Those patients, referred to as "secondary" patients, are added to the contact list.

For example, secondary patients may be identified as people who share one or more phone numbers with the primary patient, or who may otherwise be identified as having a common address or family relationship with the primary patient. Some practice management systems support the indication of family relationships as part of the patient record.

While such data is helpful, phone number matching will typically be the most reliable factor in identifying secondary patients since it does not depend on staff recognizing and correctly indicating family relationships when setting up patient records in the practice management system. In cases such as a nursing home where many unrelated people may share a phone number, surname or other family indicators may be used to refine the set of secondary patients. These cases can be recognized by a threshold for the number of patients in the set. For example, when more than 5 patients share the same phone number, those with surnames different from the primary patient are excluded from the call set.

Each secondary patient is checked to determine whether he is a qualified patient, as defined above with respect to the primary patient, and whether or not he is due for a contact from the office. If the secondary patient is not qualified or not due for a contact, the list of secondary patients is annotated in step 114 to so indicate. Checking whether the secondary patients are qualified and whether they are due for a call is preferably performed automatically without human intervention, but could be performed in part manually by the user and in part automatically.

Prompt the User to Call the Patient(s), Beginning with the First Phone Number

Figure 2:
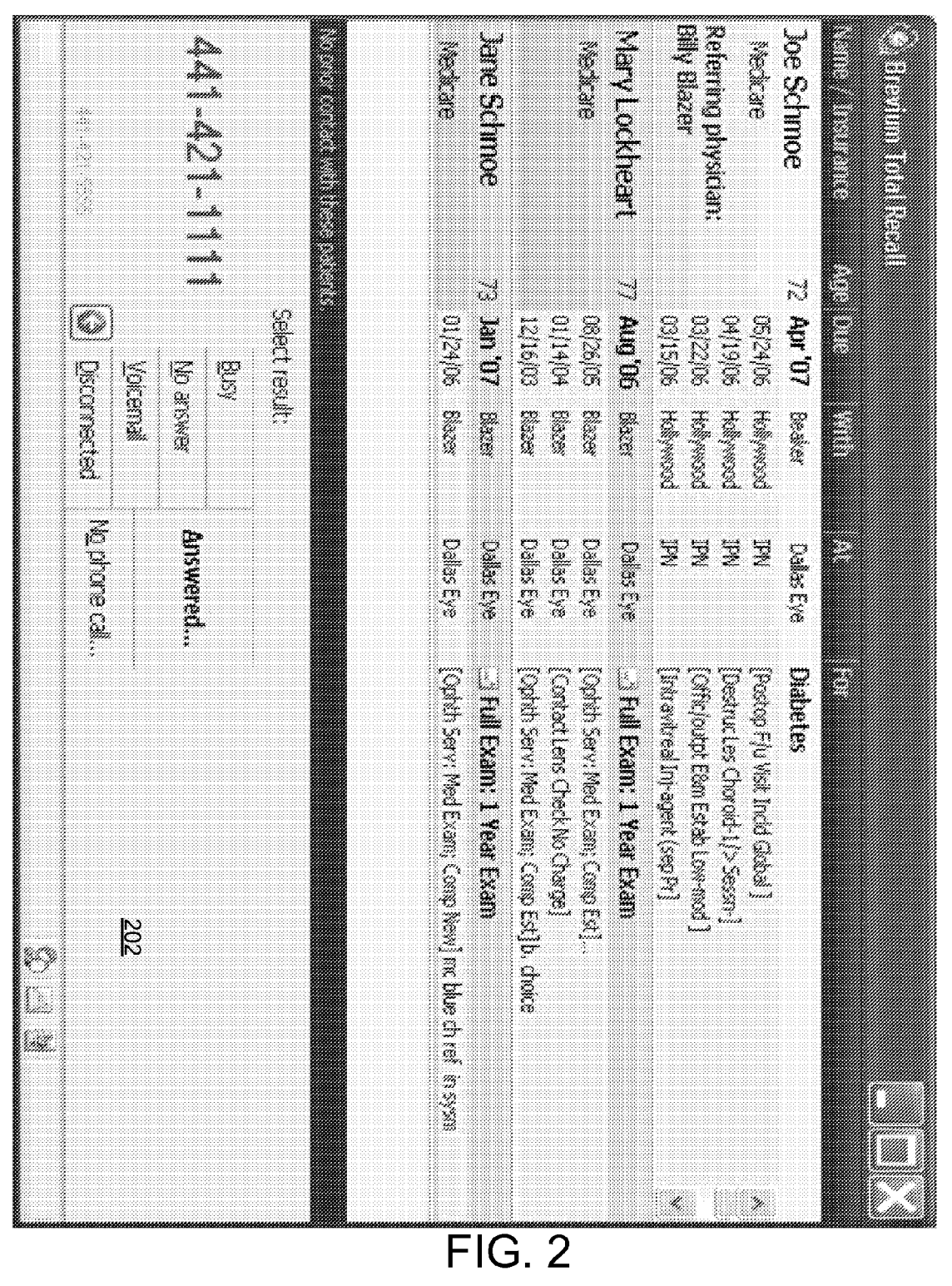

After the call set's patients and phone numbers have been qualified, the user is prompted in step 118 to call the patient(s), by displaying the first phone number to call as shown in display pane 202 of FIG. 2. In some embodiments, the system automatically dials the first number listed for the user. FIG. 2 shows that for phone number 441-421-1111, there is a primary patient, Joe Schmoe and two secondary patients, Mary Lockheart and Jane Schmoe, all having the same contact phone number. Thus, the user may be able to schedule three appointments by making one phone call. The screen shown in FIG. 2 also displays to the user other information for the primary and secondary patients that might assist the user in understanding the patients' needs and making the appointment, such as the due dates for care, reasons why visits are required, the patient's doctor, and the location for the appointment. Additional information, such as the patient's age and the appointment history, may also be displayed.

In some cases, the user may choose not to make a call. This can happen, for example, if information available to the caller (either presented by the program or available from outside the system) indicates that the patient should not be invited to make an appointment. For example, the patient's account may be in collections and his treatment elective.

Collect Call Results for the Call Set Until Results are Deemed Decisive or Phone Numbers are Exhausted The call result can be collected in a variety of ways, preferably by a human caller selecting a call result from a set of result options on the display, or less preferably, by using an automated telephone response system that can only indicate whether the call was answered and a message left. Pane 202 at the bottom of the screen of FIG. 2 provides a way for the user to enter the call results.

The call result collected for each patient is matched to a field in the "result" column of a call results table 300 (FIG. 3) in the patient reactivation system database, and certain attributes are assigned to the result based on this match. These attributes are used to determine what to do next and how long to wait before placing the patient back on the contact list for another call. For example, the "Decisive" attribute is used to determine whether to try again to contact a patient using a different phone number from the list. The "SelectType" attribute indicates whether the user needs to clarify which patients in a call set are affected by the call results. The "Timeout" attribute indicates the minimum time period after which additional contacts should be attempted, and the "Retries" attribute indicates the number of times that contact should be attempted before waiting for a more extended period to attempt contact again.

In step 130, the user enters a general call result in pane 202, and the entered result determines a value for the attribute "SelectType" from table 300. A call result may apply to one, some, or all of the patients in the call set. The "SelectType" attribute in the call results table indicates which patients in the call set the results apply to, and whether to prompt the user for clarification. For example, if the user decided not to make the phone call, the last line in Table 300 indicates that the SelectType attribute is set to "0". As shown in decision box 132, if the SelectType attribute is set to "0", then the call result is automatically applied to the primary patient in step 134. If the user selects "No answer," "Busy," "Voicemail," or "Disconnected," in pane 202, Table 300 indicates that the SelectType attribute is set to "1", and so decision block 136 shows that the result is automatically applied to all patients in the call set in step 138.

If the user clicks on "Answered" in pane 202, another screen is presented as shown in FIG. 4 that allows the user to enter the results of the conversation with the person answering the phone. For example, if Joe Schmoe answered the phone and made an appointment, the user would select "Appointment Accepted." Table 300 indicates that the SelectType attribute is set to 2. Step 142 shows that if the SelectType attribute is not set to "0" or "1", then system prompts the user to select which patient the result applies to.

Figure 6:
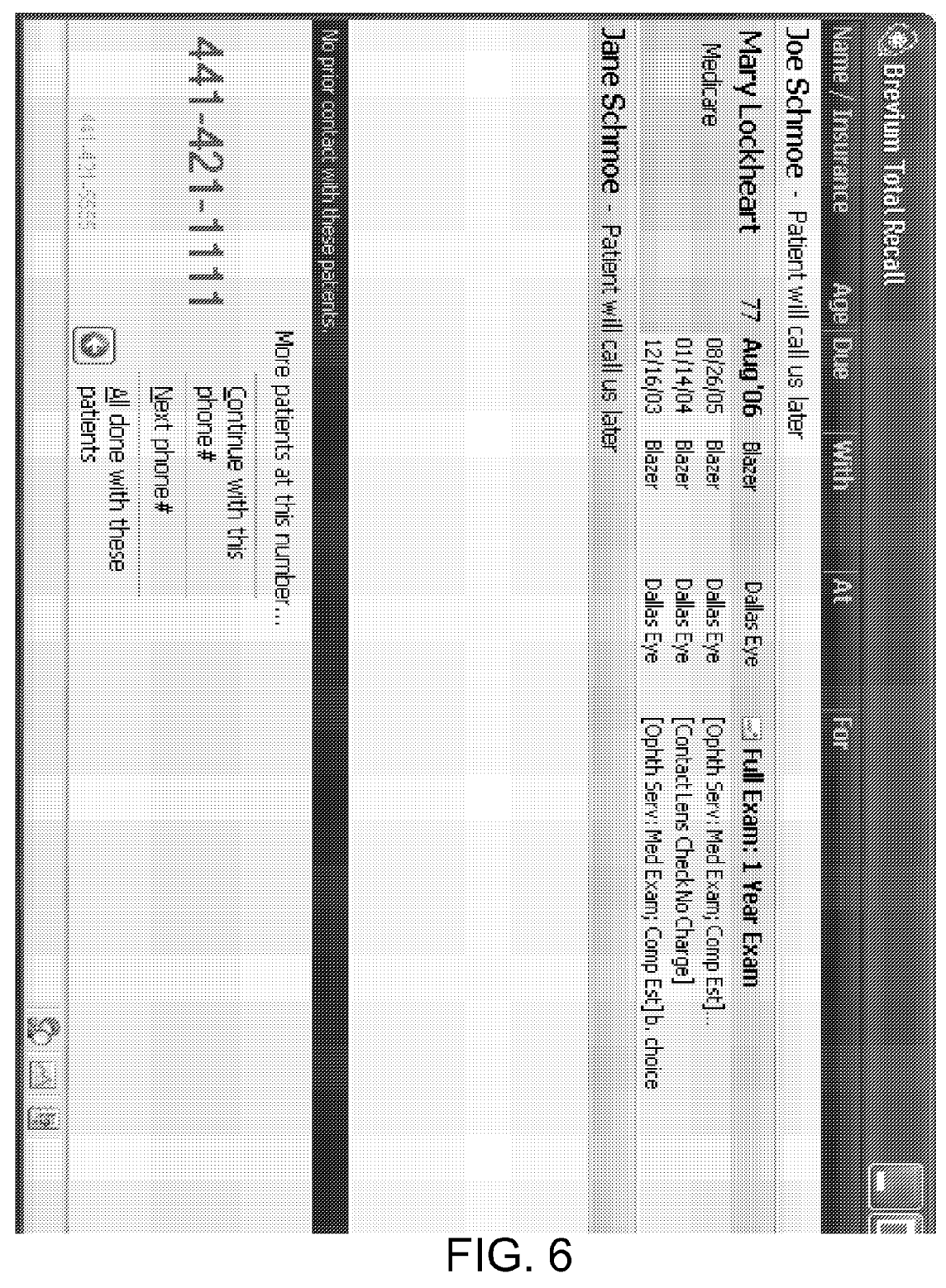

As another example, if the person answering the phone stated that she would call the office later to schedule an appointment, the user would select "Patient will call us later" from the screen in FIG. 4. The system then displays the screen in FIG. 5, which shows the previously selected "Patient will call us later" and presents a list of all patients in the call set, prompting the user to enter which patient the result applies to. FIG. 5 shows that the prompt by default has all the patients selected. The default patient selection may vary with the specific call result that was entered. The user can elect the default of all patients in the call set by clicking OK, or can uncheck any of the patients that the result does not apply to. For example, FIG. 6 shows that Jane and Joe Schmoe but not Mary Lockheart will call later, indicating that the user had unselected Mary Lockheart.

Unless the call result indicates in decision box 150 that the phone number has been disconnected or the user is instructed by the party answering the phone not to use the number, a phone follow-up time is calculated in block 159 (FIG. 1C). If the call result indicated by the user was "disconnected" or "don't use this number," then the user is prompted in block 154 to enter a new phone number, if available. If the call result was "disconnected," as shown in decision block 156 and if a new number is available, the new number is substituted in block 158 for all occurrences of the disconnected phone number in the patient reactivation system database. If the call result was "don't use this number," the user is prompted to select which patients the new number should be applied to and in block 160, and the new number is applied to the selected patients, replacing the old number.

The process continues in FIG. 1C, with the calculation of the follow-up time for selected patients in block 170. The method of calculating the follow-up time is described in more detail below. The call results for specific patients are recorded in the patient reactivation system database in step 172. If no call was made, the user clicks on the "No phone call" box in pane 202, which optionally links to a data entry box to collect the reason for not making the call, and then the process restarts back in step 102, initializing the call set and fetching a new primary patient.

If a call was made, the patients for whom the results were collected, that is, the patients selected in step 134, 138, or 142, are removed from the call set in block 176. Step 178 shows that if there are patients remaining in the call set without results, the user is asked in step 180 whether or not to continue collecting results for the remaining patients in the call set. FIG. 6 shows a display screen in which the use can decide to continue collecting results for the current phone number, move to the next phone number for the current call set, or move to a new call set. If the user decides in block 182 that he is not done with the current phone number, that is, he wants to continue to collect data for the current phone number, the set of results presented to the user is optionally modified in step 184 from those shown in pane 202 to those shown in FIG. 4 to prevent the user from entering an invalid result for the remaining patients. A visual indication can be used to indicate to the user that no more results are expected for the patients for whom results have already been collected, such as removing them from the displayed list of patients in the call set. The user returns to step 130 where he is prompted to enter the call results for a call result for the remaining patients.

After a call result has been collected for all patients in the call set, or the user indicates in step 182 that she is done with the current phone number, all patients without a "decisive" result are added back to the call set in step 188. If the primary patient had a "decisive" result and is therefore no longer in the call set as determined in decision block 190, the call is considered complete and the process begins again in step 102 with a new primary patient.

If the primary patient is still in the call set, then it is determined in step 192 if there are more phone numbers to call. If so, the user is asked in step 193 whether she is done with the call set, or whether she would like to continue with the next phone number. If she indicates in block 194 that she is not done with the call set, then the next phone number is displayed in step 196. The user calls the number and is again prompted in step 130 for a call result for the remaining patients. The "no phone call" option is hidden when the user selected the option of displaying the next phone number.

If there were not more phone numbers in decision block 192 or if block 194 indicates that the user was done with the call set, then the call group is complete.

When no decisive result is obtained for the primary patient, but a decisive result was obtained for any of the secondary patients, it is helpful for proper call spacing to assume that the secondary patient will tell the primary patient about the call. Thus, decision block 197 shows that if any of the secondary patient results were decisive, then a "message left" result is imputed in step 198 for the primary patient when no "decisive" result has been recorded for the primary patient. "Decisive" results typically imply that someone at the household actually spoke to the caller. "Imputing a message left" means that the system will assume the secondary patient will mention the call to the primary patient even if no explicit "message left" result was recorded, and space the next call accordingly. In step 199, a follow-up time is calculated for the primary patient, and the process returns to the beginning again at step 102.

Calculating Follow-Up Time for the Current Phone Number and for Selected Patients.

There are a variety of approaches possible for calculating the follow-up time. One approach is to rely solely on follow-up times associated with patients and not to use a follow-up time associated with telephone numbers. The problem with this approach is that it requires that some kind of result be stored for patients who share a phone number with others who were called, in order to avoid calling the same household again, even if the user does not enter call results for all patients in the call set. A better approach is to use the call results to calculate a follow-up time for the phone number, as follows.

After each call result is collected, if the result was anything other than "disconnected" or "don't use this number" the follow-up time for each phone number is calculated in step 159 by adding the number of days expressed by the "Timeout" attribute (FIG. 3) for the call result just collected, to the current date. The calculated phone follow-up time is compared to the existing follow-up time for that phone number, and recorded if the new follow-up time is sooner than the existing phone follow-up time, or if there is no existing follow-up time for that phone number.

As each call result is collected, patient follow-up times are calculated and recorded for each patient based on the patient's prior contact history and the Table 300 attributes associated with the call result. The number of days expressed by the "Timeout" attribute is added to the current date to determine a follow-up time. The "retries" attribute determines the number of retry attempts for that call result (or other results with an equal or greater timeout value) before a more extended timeout period is appropriate. The newly calculated patient follow-up times are compared to the existing follow-up time for each patient, and recorded if the new follow-up time is later than the existing patient follow-up time or if there is no existing follow-up time.

If the patient follow up time indicates that a call is due, but the telephone follow-up time indicates that no call should be made because the number was recently called for a different patient in the household, then the patient is not called.

Hardware Schematic

Figure 7:
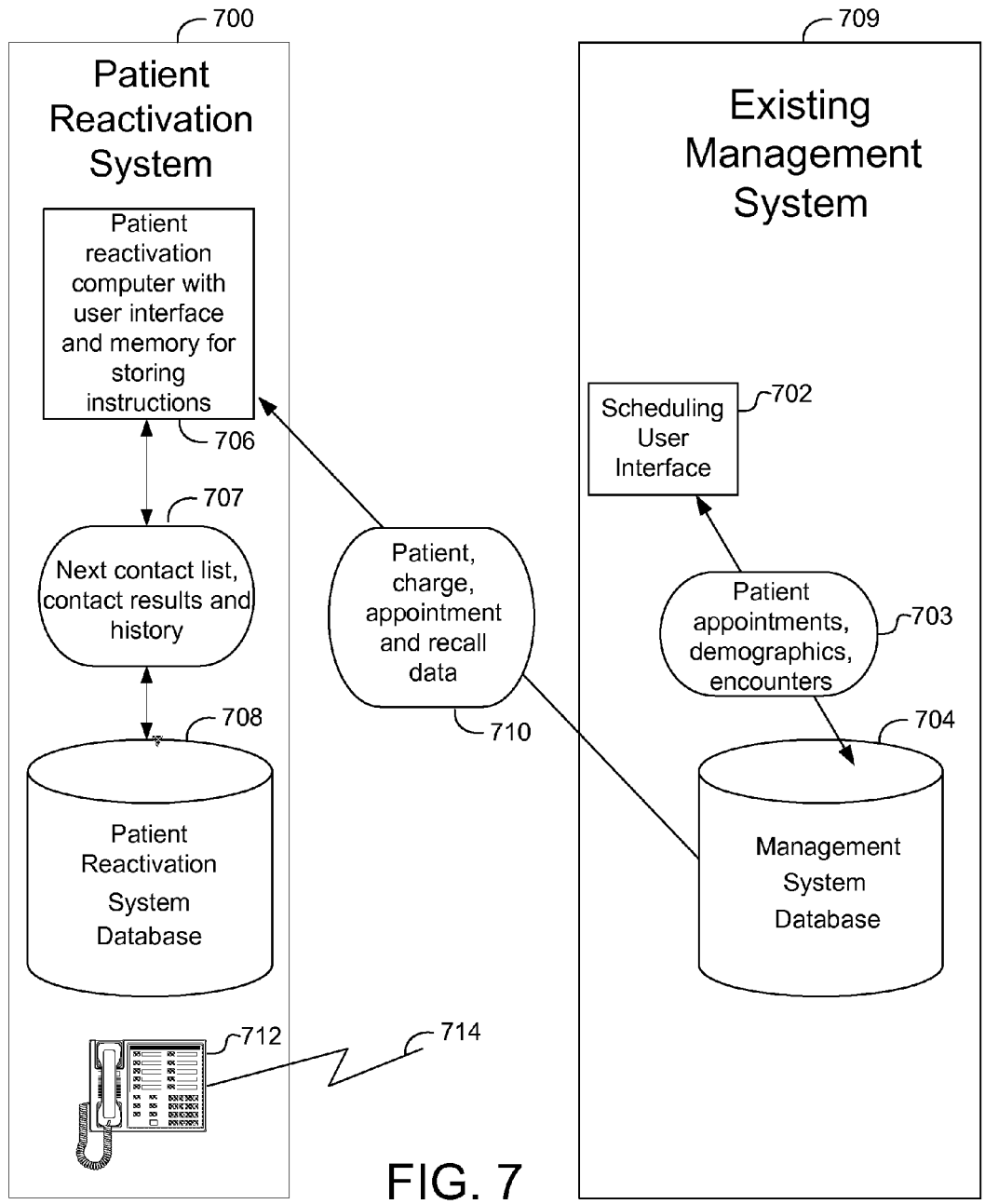
FIG. 7 shows schematically the hardware implementing the present invention.

FIG. 7 is a block diagram showing the patient reactivation system and an existing management system which can be used together to implement the invention. A patient reactivation system 700 includes a patient reactivation system user computer 706 with a user interface, including, for example, a video display by which a user can view information presented by the system about patients to be called, and a keyboard, mouse, or other device by which the user can enter data into a user computer on the system. In some embodiments, calls to patients may be automated, and made without human assistance. In preferred embodiments, calls are made by a human user in order to better relate to the patients being called. The human user uses a telephone 712 connected to a public telephone network 714 or uses a telephone interface on computer 706. Patient reactivation system 700 also includes a patient reactivation system database 708 that stores lists of patients to contact and information about the patients necessary to make the contact. Patient reactivation system database 708 may be stored on user computer 706 or on a network storage location. The patient reactivation system 700 interfaces with an existing management system 709, which includes a scheduling user interface 702 and a management system database 704 that typically includes billing codes. As described above, the billing codes can be used to determine when additional visits are required.

The scheduling user interface 702 draws patient appointments 703 from the management system database 704, and writes new appointments 703 into the management system database 704. The patient reactivation system 700 determines, as described above, patients who should be contacted 710 and prompts one or more users to contact these patients. The contact results and history 707 are stored into the patient reactivation system database 708. The patient reactivation system 700 queries the patient reactivation system database 708 to avoid contacting patients redundantly or too frequently.

While the foregoing is a detailed description of the preferred embodiment of the invention, there are many alternative embodiments of the invention that would occur to those skilled in the art and which are within the scope of the present invention. Accordingly, the present invention is to be determined by the following claims.

The invention claimed is:

1. A method for improving call yields and reducing redundant calls in a patient reactivation system used to call patients who have not scheduled an appointment to receive a needed health care service and to invite them to schedule an appointment, comprising:
   a) selecting a primary patient name from a contact list, the contact list including names of patients who have not scheduled an appointment to receive a needed health care service;
   b) automatically determining the names of one or more secondary patients from the contact list who reside in the same household as the primary patient, the primary patient and the secondary patients forming a call set;
   c) prompting the user to call the patients at the first telephone number associated with the call set;
   d) recording call results for the patients in the call set;
   e) calculating a telephone follow-up time for the first telephone number;
   f) calculating a patient follow-up time for each of the primary and secondary patients;
   g) recording the calculated telephone follow-up time if the calculated telephone follow-up time is later than an existing telephone follow-up time associated with the first telephone number or if there is no existing telephone follow-up time associated with the first telephone number; and
   h) recording each calculated patient follow-up time if the calculated patient follow-up time is later than an existing patient follow-up time associated with the patient or if there is no existing patient follow-up time associated with the patient.

2. The method according to claim 1, wherein recording call results for the patients in the call set includes recording results for the primary patient and at least one of the secondary patients.

3. The method according to claim 1, wherein calculating the telephone follow-up time includes adding a predetermined number of days associated with the recorded call result to a current date.

4. The method according to claim 1, wherein recording call results for the patients in the call set includes recording individual call results for the members of the call set.

5. The method according to claim 2 in which recording individual call results for the members of the call set includes selecting from a computer screen a call result and selecting which of the patients in the call set the selected call result applies to.

6. The method according to claim 2 in which some selected call results are automatically applied to all patients in a call set and in which some selected call result are automatically applied to the primary patient.

7. The method according to claim 1, wherein calculating the patient follow-up time includes adding a predetermined number of days associated with the recorded call result to a current date.

8. The method according to claim 1, wherein the user is prompted to call the patients at the first telephone number associated with the call set if the telephone follow-up time is not later than each of the patient follow-up times associated with patients in the call set.

9. The method according to claim 1, wherein automatically determining the names of one or more secondary patients from the contact list comprises determining the names of secondary patients sharing a telephone number with the primary patient.

10. The method according to claim 1, wherein automatically determining the names of one or more secondary patients from the contact list comprises using family relationship information from the management system to determine the names of one or more secondary patients who belong to the same family as the primary patient.

11. The method according to claim 1, further comprising using a computer-telephone interface to auto-dial the first phone number.

12. The method according to claim 1, further comprising:
   presenting to a user a second telephone number associated with the call set; and
   recording second call results for each of the patients in the call set for whom final call results were not previously recorded.

13. The method according to claim 12, further comprising calculating a follow-up time associated with the first and second telephone numbers.

14. The method according to claim 1, wherein recording call results for each of the patients in the call set includes recording a new phone number when the call results indicate that the current number is not valid.

15. The method according to claim 1, further comprising performing a last minute verification that the first patient should be contacted before prompting the user to contact the patient.

16. A patient reactivation system used to call patients who have not scheduled an appointment to receive a needed health care service, comprising a computer programmed to:
   a) select a primary patient name from a contact list, the contact list including names of patients who have not scheduled an appointment to receive a needed health care service;
   b) automatically determine the names of one or more secondary patients from the contact list who reside in the same household as the primary patient, the primary patient and the secondary patients forming a call set;
   c) prompt the user to call the patients at the first telephone number associated with the call set; and
   d) record call results for each of the patients in the call set;
   e) calculate a telephone follow-up time for the first telephone number;
   f) calculate a patient follow-up time for each of the primary and secondary patients;
   g) record the calculated telephone follow-up time if the calculated telephone follow-up time is later than an existing telephone follow-up time associated with the first telephone number or if there is no existing telephone follow-up time associated with the first telephone number; and
   h) record each calculated patient follow-up time if the calculated patient follow-up time is later than an existing patient follow-up time associated with the patient or if there is no existing patient follow-up time associated with the patient.

17. A computer-readable medium having thereon computer-readable instructions for:

a) selecting a primary patient name from a contact list, the contact list including names of patients who have not scheduled an appointment to receive a needed health care service;

b) automatically determining the names of one or more secondary patients from the contact list who reside in the same household as the primary patient, the primary patient and the secondary patients forming a call set;

c) prompting the user to call the patients at the first telephone number associated with the call set; and d) recording call results for the patients in the call set;

e) calculating a telephone follow-up time for the first telephone number;

f) calculating a patient follow-up time for each of the primary and secondary patients;

g) recording the calculated telephone follow-up time if the calculated telephone follow-up time is later than an existing telephone follow-up time associated with the first telephone number or if there is no existing telephone follow-up time associated with the first telephone number; and h) recording each calculated patient follow-up time if the calculated patient follow-up time is later than an existing patient follow-up time associated with the patient or if there is no existing patient follow-up time associated with the patient.

18. The system according to claim 16, wherein the computer prompts the user to call the patients at the first telephone number associated with the call set if the telephone follow-up time is not later than each of the patient follow-up times associated with patients in the call set.

19. The computer-readable medium according to claim 17, wherein the computer-readable instructions prompt the user to call the patients at the first telephone number associated with the call set if the telephone follow-up time is not later than each of the patient follow-up times associated with patients in the call set.

* * * * *